(12) United States Patent
Hoy, IV et al.

(10) Patent No.: US 9,765,007 B2
(45) Date of Patent: Sep. 19, 2017

(54) DEHYDRATION PROCESS

(71) Applicant: Rohm and Haas Company, Philadelphia, PA (US)

(72) Inventors: Stacy W. Hoy, IV, Houston, TX (US); Dmitri A. Kraptchetov, Collegeville, PA (US); Mark A. Silvano, Collegeville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/917,114

(22) PCT Filed: Sep. 18, 2014

(86) PCT No.: PCT/US2014/056268
§ 371 (c)(1),
(2) Date: Mar. 7, 2016

(87) PCT Pub. No.: WO2015/065610
PCT Pub. Date: May 7, 2015

(65) Prior Publication Data
US 2016/0229779 A1    Aug. 11, 2016

Related U.S. Application Data

(60) Provisional application No. 61/896,378, filed on Oct. 28, 2013.

(51) Int. Cl.
| | |
|---|---|
| *C07C 67/00* | (2006.01) |
| *C07C 45/83* | (2006.01) |
| *C07C 45/65* | (2006.01) |
| *C07C 45/80* | (2006.01) |
| *C07C 45/82* | (2006.01) |
| *C07C 45/50* | (2006.01) |
| *C07C 45/61* | (2006.01) |
| *C07C 67/44* | (2006.01) |

(52) U.S. Cl.
CPC ............ *C07C 45/83* (2013.01); *C07C 45/505* (2013.01); *C07C 45/61* (2013.01); *C07C 45/65* (2013.01); *C07C 45/80* (2013.01); *C07C 45/82* (2013.01); *C07C 67/44* (2013.01)

(58) Field of Classification Search
None
See application file for complete search history.

(56) References Cited

U.S. PATENT DOCUMENTS

| | | |
|---|---|---|
| 2,514,966 A | 7/1950 | Pierotti |
| 2,514,967 A | 7/1950 | Pierotti |
| 3,098,798 A | 7/1963 | Marks |
| 3,597,880 A | 8/1971 | Norgiel |
| 3,828,099 A | 8/1974 | Sato |
| 4,247,486 A | 1/1981 | Brewester et al. |
| 4,249,019 A | 2/1981 | Tamura et al. |
| 4,496,770 A | 1/1985 | Duembgen et al. |
| 4,518,796 A | 5/1985 | Aoshima et al. |
| 4,716,250 A | 12/1987 | Abatjoglou et al. |
| 4,731,486 A | 3/1988 | Abatjoglou et al. |
| 5,087,763 A | 2/1992 | Sorensen |
| 5,288,918 A | 2/1994 | Maher et al. |
| 5,356,460 A | 10/1994 | Vogel et al. |
| 5,892,102 A | 4/1999 | Mikami et al. |
| 5,969,178 A | 10/1999 | Okamoto et al. |
| 5,969,578 A | 10/1999 | Rust |
| 6,040,472 A | 3/2000 | Yamamatsu et al. |
| 6,107,515 A | 8/2000 | Yamaguchi et al. |
| 7,141,702 B2 | 11/2006 | Deshpande et al. |

FOREIGN PATENT DOCUMENTS

| | | |
|---|---|---|
| CN | 1817844 A | 8/2006 |
| EP | 0890569 A1 | 1/1999 |
| EP | 2740535 A1 | 6/2014 |
| GB | 825021 A | 12/1959 |
| JP | 58198442 A | 11/1983 |
| WO | 2014116588 A1 | 7/2014 |
| WO | 2015017430 A1 | 2/2015 |
| WO | 2015017436 A1 | 2/2015 |
| WO | 2015017437 A1 | 2/2015 |

*Primary Examiner* — Sudhakar Katakam
*Assistant Examiner* — Ana Z Muresan
(74) *Attorney, Agent, or Firm* — Edward L. Brant

(57) ABSTRACT

A process for preparing dry methacrolein, and a process for producing methyl methacrylate are disclosed.

16 Claims, 2 Drawing Sheets

DEHYDRATION PROCESS

BACKGROUND OF THE INVENTION

The invention relates to a process for preparing dry methacrolein, and to a process for making methyl methacrylate.

Methacrolein (MA) is a common intermediate in methyl methacrylate (MMA) production. MA can be produced from the more abundant ethylene ($C_2$) feedstock, such as via liquid phase propionaldehyde condensation as disclosed in U.S. Pat. No. 4,496,770, or from less abundant isobutylene or tert-butanol ($C_4$) feedstocks, such as via vapor phase $C_4$ oxidation as disclosed in U.S. Pat. No. 5,969,578. The methacrolein product stream contains significant amounts of water for both $C_2$- and $C_4$-based methacrolein production methods. However, water is detrimental to the subsequent oxidative esterification process, such as is disclosed in U.S. Pat. No. 5,969,178, U.S. Pat. No. 6,107,515 and U.S. Pat. No. 6,040,472, which converts methacrolein to methyl methacrylate in a single step, thus advantageously bypassing the intermediate methacrylic acid (MAA) production step of other known processes. Thus, if an MA stream from conventional processes is to be used as a feed stream for a downstream oxidative esterification process, it advantageously is first dehydrated.

U.S. Pat. No. 5,969,578 describes a method for dehydrating a gaseous methacrolein-containing product stream produced by a $C_4$ oxidation process. Water contained in the gaseous stream is removed by partial condensation, while the methanol and methacrolein components are allowed to remain gaseous. The gaseous methacrolein-containing mixture is then contacted with a very dry cooled methanol-containing stream to absorb the methacrolein. The resulting absorber bottoms product mixture contains 25-69% methacrolein in methanol, and <1% water. This mixture is sufficiently dry to feed a downstream oxidative esterification reactor. However, this scheme suffers from a number of disadvantages. For example, it carries large loads of non-condensables through multiple columns, thus requiring unfavorably large equipment, can contain large absorbent recycle streams between multiple upstream and downstream units, requires pure methanol or very dry methanol-containing absorbent streams, produces relatively dilute methacrolein, and can be sensitive to process upsets due to its heavy recycle integration between multiple units. Furthermore, while such a scheme can accommodate a dilute gaseous methacrolein stream resulting from a $C_4$ oxidation process, it is not practical for highly aqueous methacrolein streams produced in a $C_2$-based process, such as the propionaldehyde-formaldehyde condensation process described in U.S. Pat. No. 4,496,770. In fact, U.S. Pat. No. 5,969,578 discourages the use of methods involving the use of water as a contacting solvent for methacrolein production and goes to significant lengths to entirely avoid the co-condensation of water and methacrolein.

Another method of treating a gaseous methacrolein-containing product of a $C_4$ oxidation process is described in U.S. Pat. No. 3,597,880, which discloses a process in which the gaseous methacrolein containing mixture is contacted with methanol to absorb methacrolein and water. The resulting liquid mixture contains methanol, methacrolein, and a modest amount of water, e.g., 5.8% indicated in Example 1. The liquid mixture is then subjected to extractive distillation with water, where the concentration of water in a liquid phase in an absorbing section of the extractive distillation zone is controlled to a concentration of from 50 to 90 mole %. The above concentration of water is targeted in order to avoid the formation of a methacrolein-methanol azeotrope, and to enable the separation of methacrolein from excess methanol that is recycled for use in the upstream absorption step. Methacrolein is thus recovered as a top distillate, whereas the bottom liquid of the extractive distillation column is further distilled to separate methanol from water. The top distillate stream of the extractive distillation column, which is an azeotrope of water and methacrolein (azeotropic point 63.6° C.; methacrolein/water weight ratio 100/7.9, per U.S. Pat. No. 5,969,578) containing about 7% water, is allowed to phase separate to give an organic liquid phase containing mostly methacrolein and a level of water dictated by liquid-liquid equilibrium, about 3% water. The aqueous liquid phase contains mostly water and a level of methacrolein dictated by liquid-liquid equilibrium, namely about 6% methacrolein. The process, however, is not concerned with drying the methacrolein product further, thus producing methacrolein containing approximately 3% water. The patent states that the methacrolein product can be further purified by additional distillation or the like. The process is intended to capture methacrolein from a gaseous $C_4$ oxidation product stream, with the associated absorber bottoms containing mostly methanol, methacrolein, and only a modest amount of water, e.g., 5.8% water indicated in Example 1. This process is not practical for a highly-aqueous, e.g., 65% water, liquid methacrolein product stream of a propionaldehyde condensation process, such as described in U.S. Pat. No. 4,496,770, used with $C_2$ feedstock.

U.S. Pat. No. 2,514,966 and U.S. Pat. No. 2,514,967 disclose a method in which a gas that contains acrolein (or other unsaturated aldehydes) and steam is absorbed into water. This method is carried out by scrubbing an acrolein-containing gaseous mixture with a large amount of water under high pressure to form an aqueous solution containing about 2 wt % of acrolein, and then subjecting the aqueous acrolein solution to stripping, rectification and extractive distillation to recover the acrolein. Such a process is disadvantageous in that an extremely large amount of water must be used under high pressure to absorb acrolein from the gaseous reaction mixture, due to the inherently low solubility of acrolein in water (21.4 wt % under 20° C. per U.S. Pat. No. 3,957,880). This problem would be exacerbated if this method were to be applied to methacrolein, as methacrolein is even less soluble in water (6.1 wt % at 25° C.). Another disadvantage of this method is that in the acrolein separation step, an extractive distillation, is conducted at a temperature below 35° C. using a very large amount of water as a solvent. The large amount of water is required to avoid a heterogeneous extractive distillation zone, and the low temperature is required to achieve a favorable relative volatility regime for acrolein separation that otherwise would not be attained. Such operating conditions require a pressure as low as 50 mmHg. The utility cost of the acrolein separation is high due to the large amount of water used. The capital cost of the acrolein separation process is also high due to the large column diameter required to process the high water flow. These costs would be further exacerbated if this extractive distillation method were to be applied to methacrolein, since even more water (at least 94 wt % of a mixture containing methacrolein) would be required to avoid a heterogeneous extractive distillation zone due to the low solubility of methacrolein in water. Even if implemented, such a scheme would be limited by the MA:water azeotrope to yield azeotrope-like water levels in product methacrolein. Specifically, methacrolein would be recovered in the form of an azeotropic mixture of methacrolein and water [azeotropic point: 63.6° C. & 100:7.9 per U.S. Pat. No. 5,969,578]. Thus, U.S. Pat. No. 2,514,966 and U.S. Pat. No. 2,514,967 teach the importance of avoiding heterogeneous extractive distillation configurations, thus advocating high levels of water.

No desirable process for dehydrating a heavily aqueous methacrolein stream encountered in a $C_2$ based process, such as propionaldehyde condensation, has been described despite the fact that $C_2$ is a more abundant feedstock and would provide an economic advantage in many regions of the world. In view of the deficiencies of the $C_4$-based prior art and the lack of suitable methods to efficiently dehydrate heavily aqueous $C_2$-derived liquid methacrolein streams, it would be desirable to have an improved dehydration process for a $C_2$-derived liquid methacrolein stream.

SUMMARY OF THE INVENTION

The invention is such a process comprising (a) providing a first stream comprising water, methacrolein and, optionally, methanol to a phase separator, with the proviso that the first stream comprises at least 8 weight percent water; (b) allowing the first stream to phase separate into an organic phase that comprises primarily methacrolein and an aqueous phase that comprises primarily water; (c) distilling the organic phase in a dehydration column to produce a product stream comprising primarily methacrolein.

The process of the invention surprisingly produces a concentrated (>90%) methacrolein stream with less than 2 wt. % water, and avoids many disadvantages of the prior art.

In one aspect, the invention is a process for the production of MMA from ethylene, the process comprising (1) contacting ethylene with CO and $H_2$ in the presence of a hydroformylation catalyst under reaction conditions sufficient to produce propionaldehyde;

(2) contacting at least a portion of the propionaldehyde with formaldehyde in the presence of a catalyst to produce methacrolein, the methacrolein being in a first stream comprising water, the methacrolein and, optionally, methanol, with the proviso that the first stream comprises at least 10 weight percent water;

(3) providing at least a portion of the first stream to a phase separator;

(4) allowing at least a portion of the first stream to phase separate in the phase separator into an organic phase that comprises primarily methacrolein and an aqueous phase that comprises primarily water;

(5) distilling at least a portion of the organic phase in a dehydration column to produce a product stream comprising primarily methacrolein, the product stream comprising less than 2 wt % water; and (6) providing at least a portion of the product stream to a process comprising contacting the methacrolein with methanol and an oxygen-containing gas in the presence of an oxidative esterification catalyst under reaction conditions sufficient to produce MMA.

DETAILED DESCRIPTION OF THE INVENTION

Figure 1:
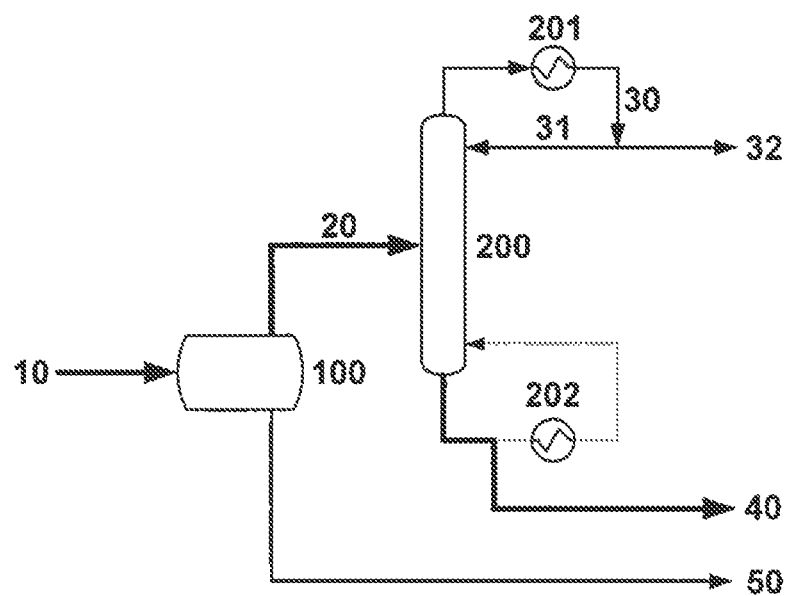
FIG. 1 is a schematic of an embodiment of the invention.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of one or more hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the use of the term "(meth)" followed by another term such as acrylate refers to both acrylates and methacrylates. For example, the term "(meth)acrylate" refers to either acrylate or methacrylate; the term "(meth) acrylic" refers to either acrylic or methacrylic; and the term "(meth)acrylic acid" refers to either acrylic acid or methacrylic acid.

As used herein, the use of the term "wppm" means parts per million by weight.

As used herein, the use of the term "fed to the top of the column" means that the relevant stream is fed to the relevant column at a point at or above the highest point of the column internals, which may comprise, e.g., packing or trays.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The process of the invention employs a wet MA feed stream. The feed stream comprises MA and water, and may contain other materials, such as residual catalyst from an upstream process. In one embodiment of the invention, the feed stream comprises at least 10 wt. % water, based upon the weight of the stream, and in other embodiments the feed stream comprises at least 20, or at least 40, wt. % water.

The source of wet methacrolein is not particularly important. The process of the invention is preferably employed with highly-aqueous $C_2$-based methacrolein streams, such as those produced from propionaldehyde by the method of U.S. Pat. No. 4,496,770. However, the process of the invention can be used to dehydrate, following condensation, dilute gaseous $C_4$-based methacrolein streams, such as those produced by the method of U.S. Pat. No. 5,969,178.

One embodiment of the invention is shown in FIG. 1. A wet MA feed stream 10 is fed to decanter 100, wherein the feed stream 10 is allowed to separate into aqueous and organic phases. The organic phase is used as the feed stream 20 to MA dehydration column 200, which is equipped with a condenser 201 and a reboiler 202. In column 200, stream 20 is distilled or stripped to remove light components, which are condensed in condenser 201. If advantageous to the operation of column 200, a portion 31 of the condensed stream can be refluxed to column 200. The condensed overhead stream 30 can be integrated into the process recycle scheme as desired. For example, at least a portion 32 of stream 30 can be recycled to decanter 100, while another portion 31 of stream 30 can be used as reflux to column 200. However, it is not necessary to use any of stream 30 as reflux, e.g., as in the case when column 200 is operated as a stripper. In another example, stream 30 can be fed to a separate decanter (not shown), whose organic product can be fed to column 200 (either via stream 20 or via reflux), and whose aqueous product can be combined with stream 50 for further processing. The bottoms stream of column 200 is recovered as the final MA product stream 40 comprising MA with a small amount of water. The MA product stream 40 can be used, in whole or in part, as a feed to other industrial chemical processes, either directly or after additional processing. For example, the MA product stream 40 can be used as a feed to an oxidative esterification process to produce MMA. The aqueous phase from decanter 100 is removed via line 50.

Figure 2:
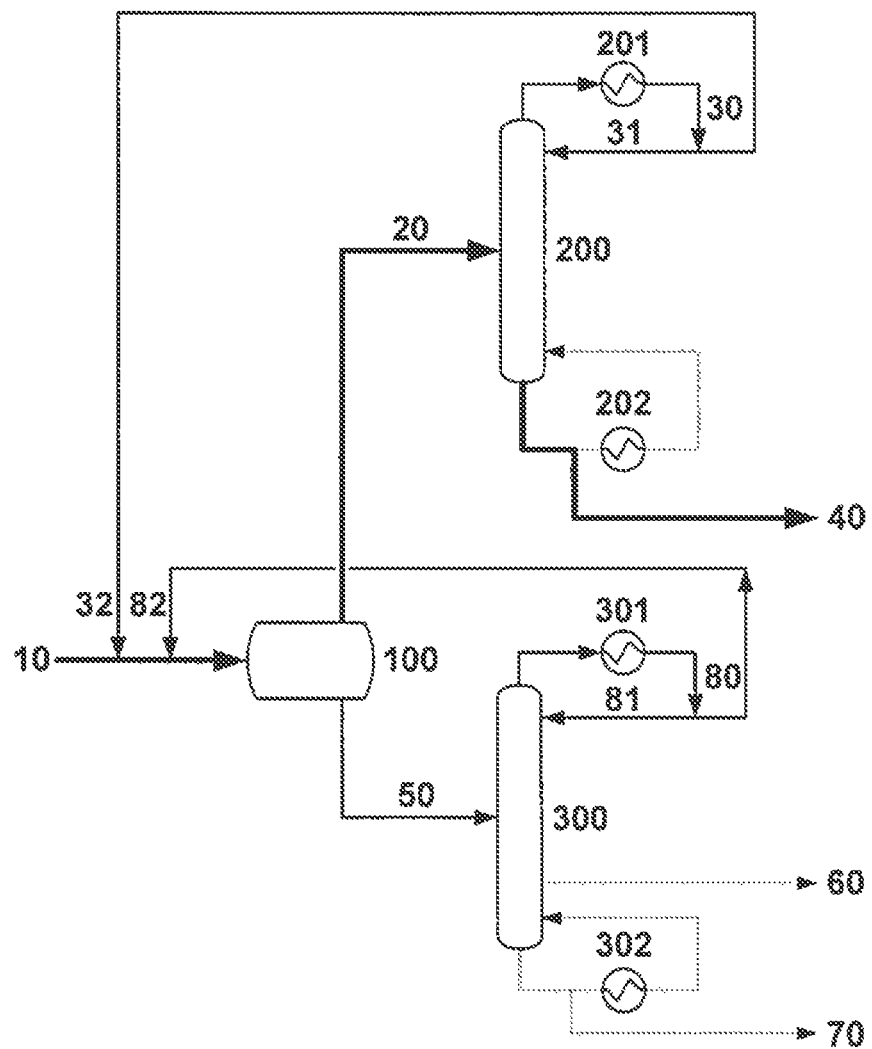
FIG. 2 is a schematic of another embodiment of the invention.

Another embodiment of the invention is shown in FIG. 2, which builds upon the process of FIG. 1. The aqueous phase from decanter 100 is sent via line 50 to water purge column 300, which is equipped with a condenser 301 and a reboiler 302. The overhead stream from column 300 is condensed in condenser 301 to produce condensed overhead stream 80, at least a portion 82 of which is recycled to decanter 100. If advantageous to the operation of column 300, a portion 81 of the condensed stream 80 can be refluxed to column 300. A water purge stream 60 is taken as a side draw stream from column 300. The bottoms stream 70 can be used as a recycle stream, either directly or after further work-up, to send material, such as catalyst, back to the reaction step that is the source of stream 10. In one embodiment of the invention, purge stream 60 is not employed and bottoms stream 70 is distilled separately to remove excess water.

Another embodiment of the invention is similar to that shown in FIG. 2, except that columns 200 and 300 are also equipped with phase separation devices, e.g., decanters, 203 and 303 (not shown) that are supplied by the liquid condensate streams leaving condensers 201 and 301, respectively. In this embodiment, a portion of the organic phase of separation device 203 is refluxed to column 200 and another portion is combined with stream 40 as MA product. The aqueous phase from device 203 is sent to phase separation device 303. Regarding device 303, its organic phase is sent to column 200, either directly or via stream 20, and its aqueous phase is refluxed to column 300.

Thus, it is possible, for the process for producing a product stream comprising primarily MA, to add the following process steps after steps (a) through (c) described hereinabove:

(d) providing to a phase separator at least part of an overhead stream from the dehydration column;

(e) distilling in a $2^{nd}$ distillation column, which can be, e.g. column 300 described hereinabove, the aqueous phase from the phase separator to produce: (1) a $2^{nd}$ distillation column bottoms stream comprising primarily water and (2) a $2^{nd}$ distillation column overhead stream; and (f) sending at least part of the $2^{nd}$ distillation column overhead stream to a phase separator.

The MA dehydration column advantageously is operated under conditions sufficient to produce an MA product stream having the desired amount of water. In one embodiment of the invention, the temperature at the bottom of the column is from 65 to 90° C. As is known to those skilled in the art, the pressure in the column will be a function of the temperature employed and the composition of the material being distilled.

The water purge column advantageously is operated under conditions sufficient to recover MA from the aqueous phase and to remove the water of reaction and undesired organic compounds from the process. In one embodiment of the invention, the temperature at the bottom of water purge column is from 80 to 110° C. As is known to those skilled in the art, the pressure in the water purge column will be a function of the temperature employed and the composition of the material being distilled.

The process of the invention advantageously does not require any methanol to achieve methacrolein dehydration, uses a single distillation column for methacrolein dehydration, and does not require a recycle from downstream process units, although recycling from downstream units is not excluded. As a result, the dehydration process of the invention is an inherently simple process that is more self-contained and robust to operation upsets in surrounding process units compared to dehydration processes of the prior art.

The process can employ any suitable equipment prepared from any suitable materials of construction, as is well known to those skilled in the art. For example, the columns can use packing, trays, or a combination of both.

The MA product stream advantageously comprises less than 2 weight percent water, based on the weight of the final MA product stream, preferably less than 1 weight percent water, and more preferably less than 0.5 weight percent water.

In one embodiment of the invention, the product MA stream is used as the feed stream to an oxidative esterification process wherein the MA is converted to MMA via the reaction of MA with methanol and an oxygen-containing gas in the presence of a catalyst. The oxidative esterification process is well known. See, e.g., U.S. Pat. No. 5,969,178, U.S. Pat. Nos. 6,107,515, 6,040,472, 5,892,102, 4,249,019, 4,518,796. In addition, U.S. Patent Application Ser. Nos. 61/859,526, 61/859,539, 61/859,544, and 61/859,551 discuss oxidative esterification and catalysts therefor.

The molar ratio of methanol employed to the amount of methacrolein employed in the MA oxidative esterification reaction, as is known to those skilled in the art, is not particularly limited, and the reaction may be conducted over a wide range of molar ratios such as 1:10 to 1,000:1, preferably from 1:1 to 10:1 methanol to methacrolein.

The oxygen-containing gas for the oxidative esterification may be either oxygen gas or a mixed gas comprising oxygen gas and a diluent inert to the reaction such as, for example, nitrogen, carbon dioxide or the like. Air may be used as the oxygen-containing gas. The quantity of oxygen present in the reaction system advantageously is not less than the stoichiometric quantity required for the reaction, and preferably is not less than 1.2 times the stoichiometric quantity. Hydrogen peroxide may be introduced into the reaction system as an oxidizer.

Catalysts that can be used for the MA oxidative esterification are well known to those skilled in the art, including palladium-based, gold-based, and other intermetallics containing combinations of two or more metals. The catalytic elements are typically present in the reaction system in such a form that they can have some interaction with each other. The oxidative esterification patents cited hereinabove give several examples of suitable oxidative esterification catalysts.

The catalytic elements may be supported on a carrier, such as silica or alumina, and the amount of the catalytic constituents supported on the carrier advantageously may be from 0.1 to 20% by weight, preferably 1 to 10% by weight, based on the weight of the carrier. Examples of suitable carriers include silica, alpha alumina and gamma alumina. The carrier may be modified, as is known by those skilled in the art. For example, a silica carrier may be modified with alumina and/or magnesia. Combinations of carriers may be employed. The catalyst constituents may also be used in the metallic form or in the form of compounds without supporting them on a carrier.

The oxidative esterification catalyst is employed in a catalytic amount. The amount of the catalyst, i.e., catalytic elements and optional carrier, may be varied freely depending on the kind and amount of the starting materials, the method of preparing the catalyst, process operating conditions and the like, although the weight ratio of catalyst to the starting MA generally is from 1:1000 to 20:1. Advantageously, the weight ratio of catalyst to MA is from 1:100 to 2:1. However, the catalyst may be used in an amount outside this range.

The oxidative esterification reaction may be conducted at a temperature of from 0° C. to 120° C., preferably from 40° C. to 90° C. Although the reaction may be conducted at reduced pressure, at atmospheric pressure, or at superatmospheric pressure, it is possible to produce the desired product by a very simple method of blowing the oxygen-containing gas into the reaction system at ambient pressure. The reaction may be conducted in a batch, semi-batch or continuous manner Advantageously, the reaction is conducted in the liquid phase.

A polymerization inhibitor can be employed in the process when the product and/or reactants comprise one or more polymerizable compounds. A wide variety of inhibitors are known and commercially available.

In one embodiment of the invention, the first stream comprising water, methacrolein and, optionally, methanol, comes from a process that converts propionaldehyde to MA. The process for converting propionaldehyde to MA via Mannich condensation with formaldehyde in the presence of an amine or amine-acid catalyst in the liquid phase is well known to those skilled in the art. See, e.g., U.S. Pat. Nos. 4,496,770 and 7,141,702. For example, Mannich condensation of propionaldehyde and formaldehyde to methacrolein can be carried out in the presence of a secondary amine, e.g., dimethylamine, and in the presence or absence of an acid, e.g., acetic acid. The reaction can be carried out under any suitable conditions at which the reaction proceeds. For example, the reaction can be conducted at a temperature of at least 20° C. and at least atmospheric pressure. In one embodiment of the invention, the reaction is conducted in the liquid phase at above 150° C., e.g., 160-210° C., and at superatmospheric pressure, e.g., 40-80 bar. The molar ratio of propionaldehyde to formaldehyde is not particularly limited, but advantageously can be maintained at around 1:1. The reaction residence time preferably is not more than 25 minutes, and more preferably is from 0.05 to 0.3 minutes, e.g., 9 seconds. The molar ratio of the amine to the acid is preferably such that the resulting pH is from 2.5 to 7.

In one embodiment of the invention, the propionaldehyde used as a feedstock for preparing MA is prepared by the hydroformylation of ethylene. The hydroformylation process is well known. See, e.g., U.S. Pat. Nos. 4,247,486, 5,087,763, 4,716,250, 4,731,486, and 5,288,918. It involves contacting an olefin with CO and hydrogen in the presence of a hydroformylation catalyst under reaction conditions sufficient to produce the corresponding aldehyde(s). In the case of ethylene, the corresponding aldehyde is propionaldehyde.

Hydroformylation catalysts are well known and any suitable such catalyst may be employed. The hydroformylation catalyst advantageously comprises a metal-organophosphorous ligand complex. Suitable organophosphorous ligands include organophosphines, organophosphites, and organophosphoramidites. The organophosphine may be a triorganophosphine such as, for example, triphenylphosphine, tris-p-tolylphosphine, tris-p-methoxyphenylphosphine, cyclohexyldiphenylphosphine, dicyclohexyldiphenylphosphine, tribenzylphosphine and the like; as well as alkali and alkaline earth metal salts of sulfonated triphenylphospines such as, for example salts of (tri-m-sulfophenyl)phosphine and of (m-sulfophenyl)diphenylphosphine and the like. Organophosphites that may serve as the ligand include monoorganophosphites, diorganophosphites, and triorganophosphites, and their use and preparation are well known in the art. Examples of illustrative organophosphoramidites may be found in EP 2 740 535.

The reaction conditions of the hydroformylation process are also well known and may include any suitable hydroformylation conditions employed for producing aldehydes. The total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1.

In general, the hydroformylation process may be conducted at any operable reaction temperature. Advantageously, the hydroformylation process is conducted at a reaction temperature from −25° C. to 200° C., preferably from 50° C. to 120° C.

In one aspect, the invention is a process for the production of MMA from ethylene, the process comprising (1) contacting ethylene with CO and $H_2$ in the presence of a hydroformylation catalyst under reaction conditions sufficient to produce propionaldehyde;

(2) contacting at least a portion of the propionaldehyde with formaldehyde in the presence of a catalyst to produce methacrolein, the methacrolein being in a first stream comprising water, the methacrolein and, optionally, methanol, with the proviso that the first stream comprises at least 10 weight percent water;

(3) providing at least a portion of the first stream to a phase separator;

(4) allowing at least a portion of the first stream to phase separate in the phase separator into an organic phase that comprises primarily methacrolein and an aqueous phase that comprises primarily water;

(5) distilling at least a portion of the organic phase in a dehydration column to produce a product stream comprising primarily methacrolein, the product stream comprising less than 2 wt % water; and (6) providing at least a portion of the product stream to a process comprising contacting the methacrolein with methanol and an oxygen-containing gas in the presence of an oxidative esterification catalyst under reaction conditions sufficient to produce MMA.

For the purposes of the invention, it is to be understood that in each of the process steps mentioned above, the process unit operations involved may be less than 100% efficient and may involve less than complete conversion of starting materials to desired products, e.g., some by-products may be produced, as would be expected by one skilled in the art, or a separation step may provide less than a perfect separation of components of its feed stream.

SPECIFIC EMBODIMENTS OF THE INVENTION

The following examples are given to illustrate the invention and should not be construed as limiting its scope.

Example 1

A liquid methacrolein reactor effluent comprising 31.2% methacrolein, 61.2% water, 4.1% methanol, 0.9% dimethylamine, 1.3% acetic acid, 600 wppm hydroquinone and 600 wppm phenothiazine is fed at 671 g/h into a liquid-liquid decanter. The temperature and pressure of the decanter are 5° C. and 1 atm, respectively. The feed splits into two phases in the decanter, with an organic to aqueous phase mass ratio of ca. 1:2.5. The organic phase effluent from the decanter, comprising 94.8% methacrolein, 2.8% water and 0.9% methanol, is accumulated.

The accumulated organic phase effluent from the decanter is fed to a methacrolein dehydration column at a rate of 760 g/h. The dehydration column is a glass, 20 tray, 33 mm Oldershaw column equipped with a forced circulation reboiler and an overhead chilled water cooled condenser. The organic phase effluent from the decanter is fed to the dehydration column at the top tray and no reflux is returned to the column; thus, the dehydration column is operated as a stripper Inhibitor consisting of 2% hydroquinone and 2% phenothiazine dissolved in the same organic phase effluent from the decanter is pumped to the overhead condenser at the rate of 6.5 g/h. The column is operated continuously for a period of 4 h at a condenser pressure of 7.7 psig and a bottoms temperature of ca. 80° C. The bottoms product comprises ca. 98% methacrolein, 0.5% methanol, and 0.2% water. The weight ratio of bottoms product to column feed is 0.66:1.

The aqueous phase effluent of the decanter is accumulated for subsequent treatment.

The example demonstrates that the process of this invention is effective at drying a methacrolein stream with a high amount of water to produce a product stream with a high methacrolein concentration and a low water concentration. Surprisingly, the water concentration in the methacrolein product stream is substantially lower than that achieved by the various methods of the prior art.

What is claimed is:

1. A process comprising
   (a) providing a first stream comprising water, methacrolein, methanol, dimethylamine, and acetic acid to a phase separator, with the proviso that the first stream comprises at least 8 weight percent water;
   (b) allowing the first stream to phase separate into an organic phase that comprises primarily methacrolein and an aqueous phase that comprises primarily water;
   (c) distilling the organic phase in a dehydration column to produce a product stream comprising primarily methacrolein.

2. The process of claim 1 wherein the first stream is primarily a liquid stream and comprises at least 10 weight percent water.

3. The process of claim 1 wherein the product stream comprises less than 2 weight percent water based on the weight of the product stream.

4. The process of claim 1 wherein the product stream comprises less than 1 weight percent water based on the weight of the product stream.

5. The process of claim 1 wherein the product stream comprises less than 0.5 weight percent water based on the weight of the product stream.

6. The process of claim 1 wherein the product stream is recovered as a side draw stream or as a bottoms stream of the dehydration column.

7. The process of claim 1 wherein an overhead stream is taken from the dehydration column, and wherein the process further comprises (d) sending at least part of the dehydration column overhead stream to a phase separator.

8. The process of claim 1 wherein the product stream is recovered as a bottoms stream of the dehydration column.

9. The process of claim 1 wherein the dehydration column is operated as a stripper.

10. The process of claim 1 further comprising providing the product stream to a process comprising contacting methacrolein with methanol and an oxygen-containing gas in the presence of a catalyst under reaction conditions sufficient to produce MMA.

11. The process of claim 1 wherein the first stream is prepared by converting propionaldehyde to methacrolein.

12. The process of claim 11 wherein the propionaldehyde is produced, at least in part, by contacting ethylene with CO and $H_2$ in the presence of a hydroformylation catalyst under reaction conditions sufficient to produce the propionaldehyde.

13. The process of claim 7 further comprising:
   (e) distilling in a $2^{nd}$ distillation column the aqueous phase from the phase separator to produce (1) a $2^{nd}$ distillation column bottoms stream comprising primarily water and (2) a $2^{nd}$ distillation column overhead stream;
   (f) sending at least part of the $2^{nd}$ distillation column overhead stream to a phase separator.

14. A process for the preparation of methyl methacrylate, the process comprising:
   (1) contacting ethylene with CO and $H_2$ in the presence of a hydroformylation catalyst under reaction conditions sufficient to produce propionaldehyde;
   (2) contacting at least a portion of the propionaldehyde with formaldehyde in the presence of a catalyst to produce methacrolein, the methacrolein being in a first stream comprising water, the methacrolein, methanol, dimethylamine, and acetic acid, with the proviso that the first stream comprises at least 10 weight percent water;
   (3) providing at least a portion of the first stream to a phase separator;
   (4) allowing at least a portion of the first stream to phase separate in the phase separator into an organic phase that comprises primarily methacrolein and an aqueous phase that comprises primarily water;
   (5) distilling at least a portion of the organic phase in a dehydration column to produce a product stream comprising primarily methacrolein, the product stream comprising less than 2 wt % water; and (6) providing at least a portion of the product stream to a process comprising contacting the methacrolein with methanol and an oxygen-containing gas in the presence of an oxidative esterification catalyst under reaction conditions sufficient to produce methyl methacrylate.

15. The process of claim 14 wherein the product stream comprises less than 0.5 weight percent water based on the weight of the product stream.

16. The process of claim 1 wherein the organic phase is fed to the top half of the dehydration column, preferably to the top of the dehydration column.

* * * * *